United States Patent
Jenkins et al.

(10) Patent No.: US 10,071,363 B2
(45) Date of Patent: Sep. 11, 2018

(54) NON-VISIBLE ACTIVATED CARBON IN ABSORBENT MATERIALS

(71) Applicant: The Clorox Company, Oakland, CA (US)

(72) Inventors: Dennis B. Jenkins, Pleasanton, CA (US); Smita S. Muddana, Kennesaw, GA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 13/781,045

(22) Filed: Feb. 28, 2013

(65) Prior Publication Data

US 2013/0177620 A1      Jul. 11, 2013

Related U.S. Application Data

(63) Continuation of application No. 12/625,259, filed on Nov. 24, 2009.

(51) Int. Cl.
| | |
|---|---|
| *B01J 20/28* | (2006.01) |
| *A61L 9/014* | (2006.01) |
| *B01J 20/10* | (2006.01) |
| *B01J 20/12* | (2006.01) |
| *B01J 20/16* | (2006.01) |
| *B01J 20/20* | (2006.01) |
| *B01J 20/30* | (2006.01) |

(52) U.S. Cl.
CPC ......... *B01J 20/28004* (2013.01); *A61L 9/014* (2013.01); *B01J 20/10* (2013.01); *B01J 20/12* (2013.01); *B01J 20/165* (2013.01); *B01J 20/20* (2013.01); *B01J 20/2803* (2013.01); *B01J 20/3007* (2013.01); *B01J 20/3028* (2013.01); *B01J 2220/42* (2013.01); *B01J 2220/4825* (2013.01); *B01J 2220/4831* (2013.01); *B01J 2220/49* (2013.01)

(58) Field of Classification Search
None
See application file for complete search history.

(56) References Cited

U.S. PATENT DOCUMENTS

| | | | |
|---|---|---|---|
| 29,783 A | 8/1860 | Harris | |
| 33,983 A | 12/1861 | Cauhaupe | |
| 3,029,783 A | 4/1962 | Sawyer, Jr. et al. | |
| 3,059,615 A | 10/1962 | Kuceski et al. | |
| 3,776,188 A | 12/1973 | Komakine | |
| 3,789,797 A | 2/1974 | Brewer | |
| 3,821,346 A | 6/1974 | Batley, Jr. | |
| 3,892,846 A | 7/1975 | Wortham | |
| 3,898,324 A | 8/1975 | Komakine | |
| 3,993,584 A | 11/1976 | Owen et al. | |
| 4,059,545 A | 11/1977 | Corbett et al. | |
| 4,085,704 A | 4/1978 | Frazier | |
| 4,187,803 A | 2/1980 | Valenta | |
| 4,256,728 A | 3/1981 | Nishino et al. | |
| 4,263,873 A | 4/1981 | Christianson | |
| 4,275,684 A | 6/1981 | Kramer et al. | |
| 4,306,516 A | 12/1981 | Currey | |
| 4,407,231 A | 10/1983 | Colbom et al. | |
| 4,437,429 A | 3/1984 | Goldstein et al. | |
| 4,506,628 A | 3/1985 | Stockel | |
| 4,517,308 A | 5/1985 | Ehlenz et al. | |
| 4,560,527 A | 12/1985 | Harke et al. | |
| 4,565,794 A | 1/1986 | de Buda | |
| 4,568,453 A | 2/1986 | Lowe, Jr. | |
| 4,591,581 A | 5/1986 | Crampton et al. | |
| 4,607,594 A | 8/1986 | Thacker | |
| 4,621,011 A | 11/1986 | Fleischer et al. | |
| 4,638,763 A | 1/1987 | Greenberg | |
| 4,641,605 A | 2/1987 | Gordon | |
| 4,657,881 A | 4/1987 | Crampton et al. | |
| 4,664,843 A | 5/1987 | Burba, III et al. | |
| 4,677,086 A | 6/1987 | McCue et al. | |
| 4,704,989 A | 11/1987 | Rosenfeld | |
| 4,721,059 A | 1/1988 | Lowe et al. | |
| 4,793,837 A | 12/1988 | Pontius | |
| 4,824,810 A | 4/1989 | Lang et al. | |
| 4,837,020 A | 6/1989 | Mise et al. | |
| 4,844,010 A | 7/1989 | Ducharme et al. | |
| 4,866,023 A | 9/1989 | Ritter et al. | |
| 4,881,490 A | 11/1989 | Ducharme et al. | |
| 4,914,066 A | 4/1990 | Woodrum | |
| 4,920,090 A | 4/1990 | Ritter et al. | |
| 4,949,672 A | 8/1990 | Ratcliff et al. | |
| 5,005,115 A | 3/1991 | Hughes | |

(Continued)

FOREIGN PATENT DOCUMENTS

| | | |
|---|---|---|
| EP | 0573303 A1 | 12/1993 |
| EP | 0716806 A1 | 6/1996 |

(Continued)

*Primary Examiner* — David J Blanchard
*Assistant Examiner* — Daniel F. Coughlin
(74) *Attorney, Agent, or Firm* — Ann Lee

(57) ABSTRACT

The present invention teaches an absorbent material with powdered activated carbon which is substantially light-colored without using color masking agents or hiding. This invention addresses the need in the field for an absorbent material with improved odor-controlling properties, that maintains such properties for longer periods of time and where the absorbent material maintains a light-colored appearance without the addition of color-masking agents. Suitable methods for creating the absorbent materials include a pan agglomeration process, a high shear agglomeration process, a low shear agglomeration process, a high pressure agglomeration process, a low pressure agglomeration process, a rotary drum agglomeration process, a pan agglomeration process, a roll press compaction process, a pin mixer process, a dry blending process, a spray coating process, an extrusion process, a pelletizing process and a fluid bed process.

18 Claims, 1 Drawing Sheet

(56) References Cited

U.S. PATENT DOCUMENTS

| | | |
|---|---|---|
| 5,005,520 A | 4/1991 | Michael |
| 5,013,335 A | 5/1991 | Marcus |
| 5,014,650 A | 5/1991 | Sowle et al. |
| 5,018,482 A | 5/1991 | Stanislowski et al. |
| 5,019,254 A | 5/1991 | Abrevaya et al. |
| 5,032,549 A | 7/1991 | Lang et al. |
| 5,062,383 A | 11/1991 | Nelson |
| 5,079,201 A | 1/1992 | Chu et al. |
| 5,094,189 A | 3/1992 | Aylen et al. |
| 5,094,190 A | 3/1992 | Ratcliff et al. |
| 5,100,600 A | 3/1992 | Keller et al. |
| 5,101,771 A | 4/1992 | Goss |
| 5,109,805 A | 5/1992 | Baldry et al. |
| 5,129,365 A | 7/1992 | Hughes |
| 5,135,743 A | 8/1992 | Stanislowski et al. |
| 5,143,023 A | 9/1992 | Kuhns |
| 5,146,877 A | 9/1992 | Jaffee et al. |
| 5,152,250 A | 10/1992 | Loeb |
| 5,176,107 A | 1/1993 | Buschur |
| 5,176,108 A | 1/1993 | Jenkins et al. |
| 5,176,879 A | 1/1993 | White et al. |
| 5,183,010 A | 2/1993 | Raymond et al. |
| 5,183,655 A | 2/1993 | Stanislowski et al. |
| 5,188,064 A | 2/1993 | House |
| 5,193,489 A | 3/1993 | Hardin |
| 5,196,473 A | 3/1993 | Valenta et al. |
| 5,204,310 A | 4/1993 | Tolles et al. |
| 5,206,207 A | 4/1993 | Tolles |
| 5,207,830 A | 5/1993 | Cowan et al. |
| 5,210,112 A | 5/1993 | Shimoda et al. |
| 5,230,305 A | 7/1993 | House |
| 5,232,627 A | 8/1993 | Burba, III et al. |
| 5,238,470 A | 8/1993 | Tolles et al. |
| 5,250,491 A | 10/1993 | Yan |
| 5,276,000 A | 1/1994 | Mathews et al. |
| 5,279,259 A | 1/1994 | Rice et al. |
| 5,304,527 A | 4/1994 | Dimitri |
| 5,317,990 A | 6/1994 | Hughes |
| 5,318,953 A | 6/1994 | Hughes |
| 5,320,066 A | 6/1994 | Gunter |
| 5,325,816 A | 7/1994 | Pattengill et al. |
| 5,329,880 A | 7/1994 | Pattengill et al. |
| 5,339,769 A | 8/1994 | Toth et al. |
| 5,345,787 A | 9/1994 | Piltingsrud |
| 5,359,961 A | 11/1994 | Goss et al. |
| 5,361,719 A | 11/1994 | Kiebke |
| 5,386,803 A | 2/1995 | Hughes |
| 5,389,325 A | 2/1995 | Bookbinder et al. |
| 5,407,442 A | 4/1995 | Karapasha |
| 5,421,291 A | 6/1995 | Lawson et al. |
| 5,450,817 A | 9/1995 | Hahn et al. |
| 5,452,684 A | 9/1995 | Elazier-Davis et al. |
| 5,458,091 A | 10/1995 | Pattengill et al. |
| 5,469,809 A | 11/1995 | Coleman |
| 5,480,584 A | 1/1996 | Urano et al. |
| 5,503,111 A | 4/1996 | Hughes |
| 5,529,022 A | 6/1996 | Nelson |
| 5,538,932 A | 7/1996 | Yan et al. |
| 5,542,374 A | 8/1996 | Palmer, Jr. |
| 5,566,642 A | 10/1996 | Ochi |
| 5,577,463 A | 11/1996 | Elazier-Davis et al. |
| 5,579,722 A | 12/1996 | Yamamoto et al. |
| 5,609,123 A | 3/1997 | Luke et al. |
| 5,634,431 A | 6/1997 | Reddy et al. |
| 5,638,770 A | 6/1997 | Peleties |
| 5,647,300 A | 7/1997 | Tucker |
| 5,648,306 A | 7/1997 | Hahn et al. |
| 5,655,480 A | 8/1997 | Steckel |
| 5,664,523 A | 9/1997 | Ochi et al. |
| 5,680,830 A | 10/1997 | Kawaguchi et al. |
| 5,691,270 A | 11/1997 | Miller |
| 5,735,232 A | 4/1998 | Lang et al. |
| 5,736,481 A | 4/1998 | Miller |
| 5,736,485 A | 4/1998 | Miller |
| 5,740,761 A | 4/1998 | Lee et al. |
| 5,743,213 A | 4/1998 | Fujijura |
| 5,762,023 A | 6/1998 | Carter |
| 5,775,259 A | 7/1998 | Tucker |
| 5,806,462 A | 9/1998 | Parr |
| 5,826,543 A | 10/1998 | Raymond et al. |
| 5,836,263 A | 11/1998 | Goss et al. |
| 5,860,391 A | 1/1999 | Maxwell et al. |
| 5,863,858 A | 1/1999 | Miller et al. |
| 5,901,661 A | 5/1999 | Pattengill et al. |
| 5,944,704 A | 8/1999 | Guarracino et al. |
| 5,970,915 A | 10/1999 | Schlueter et al. |
| 5,975,019 A | 11/1999 | Goss et al. |
| 5,992,351 A | 11/1999 | Jenkins |
| 6,019,063 A | 2/2000 | Haubensak et al. |
| 6,025,319 A | 2/2000 | Surutzidis et al. |
| 6,030,565 A | 2/2000 | Golan |
| 6,039,004 A | 3/2000 | Goss et al. |
| 6,080,908 A | 6/2000 | Guarracino et al. |
| 6,089,189 A | 7/2000 | Goss et al. |
| 6,089,190 A | 7/2000 | Jaffee et al. |
| 6,101,978 A | 8/2000 | Steckel |
| 6,194,065 B1 | 2/2001 | Golan |
| 6,206,947 B1 | 3/2001 | Evan et al. |
| 6,216,634 B1 | 4/2001 | Kent et al. |
| 6,220,206 B1 | 4/2001 | Sottillo et al. |
| 6,260,511 B1 | 7/2001 | Hsu |
| 6,276,300 B1 | 8/2001 | Lewis, II et al. |
| 6,287,550 B1 | 9/2001 | Trinh et al. |
| 6,294,118 B1 | 9/2001 | Huber et al. |
| 6,308,658 B1 | 10/2001 | Steckel |
| 6,319,342 B1 | 11/2001 | Riddell |
| 6,371,050 B1 | 4/2002 | Mochizuki |
| 6,405,677 B2 | 6/2002 | McPherson et al. |
| 6,405,678 B2 | 6/2002 | Ikegami et al. |
| 6,426,325 B1 | 7/2002 | Dente et al. |
| 6,472,343 B1 | 10/2002 | McCrae et al. |
| 6,499,984 B1 | 12/2002 | Ghebre-Sellassie et al. |
| 6,543,385 B2 | 4/2003 | Raymond |
| 6,578,521 B2 | 6/2003 | Raymond et al. |
| 6,740,406 B2 | 5/2004 | Hu et al. |
| 7,603,964 B2 | 10/2009 | Jenkins et al. |
| 2001/0018308 A1 | 8/2001 | Quick et al. |
| 2001/0049514 A1 | 12/2001 | Dodge, II et al. |
| 2002/0000207 A1 | 1/2002 | Ikegami |
| 2002/0007800 A1 | 1/2002 | Ochi et al. |
| 2002/0014209 A1 | 2/2002 | Bloomer |
| 2002/0054919 A1 | 5/2002 | Hochwalt et al. |
| 2002/0117117 A1 | 8/2002 | Raymond et al. |
| 2002/0153311 A1 | 10/2002 | Farquhar Davidson |
| 2002/0183201 A1 | 12/2002 | Barnwell et al. |
| 2003/0051673 A1 | 3/2003 | Raymond et al. |
| 2003/0072733 A1 | 4/2003 | McGee et al. |
| 2003/0131799 A1 | 7/2003 | Wong et al. |
| 2003/0148100 A1 | 8/2003 | Greene et al. |
| 2007/0289543 A1 | 12/2007 | Petska et al. |

FOREIGN PATENT DOCUMENTS

| | | |
|---|---|---|
| EP | 0885557 B1 | 12/1998 |
| EP | 0579764 B1 | 8/1999 |
| EP | 0612533 B1 | 11/1999 |
| EP | 0759323 B1 | 7/2001 |
| EP | 1346634 A2 | 9/2003 |
| JP | S62-239932 A | 10/1987 |
| JP | 04287626 A | 3/1991 |
| JP | 03078627 | 4/1991 |
| JP | 05160351 A | 6/1993 |
| JP | 6-14669 A | 1/1994 |
| JP | 6343362 A | 12/1994 |
| JP | 07-041202 | 8/1996 |
| JP | 10262482 A | 10/1998 |
| WO | 9009099 A1 | 8/1990 |
| WO | 9602129 A1 | 2/1996 |
| WO | 9812291 A2 | 3/1998 |
| WO | 9827261 A2 | 6/1998 |
| WO | 9933335 A2 | 7/1999 |
| WO | 9940776 A2 | 8/1999 |
| WO | 9945764 A1 | 9/1999 |
| WO | 0037020 A2 | 6/2000 |

(56) References Cited

FOREIGN PATENT DOCUMENTS

| WO | 0119177 A1 | 3/2001 |
|----|------------|--------|
| WO | 0158521 A1 | 8/2001 |
| WO | 02056673 A2 | 7/2002 |
| WO | 02060496 A2 | 8/2002 |
| WO | 03032719 A2 | 4/2003 |
| WO | 03065796 A2 | 8/2003 |

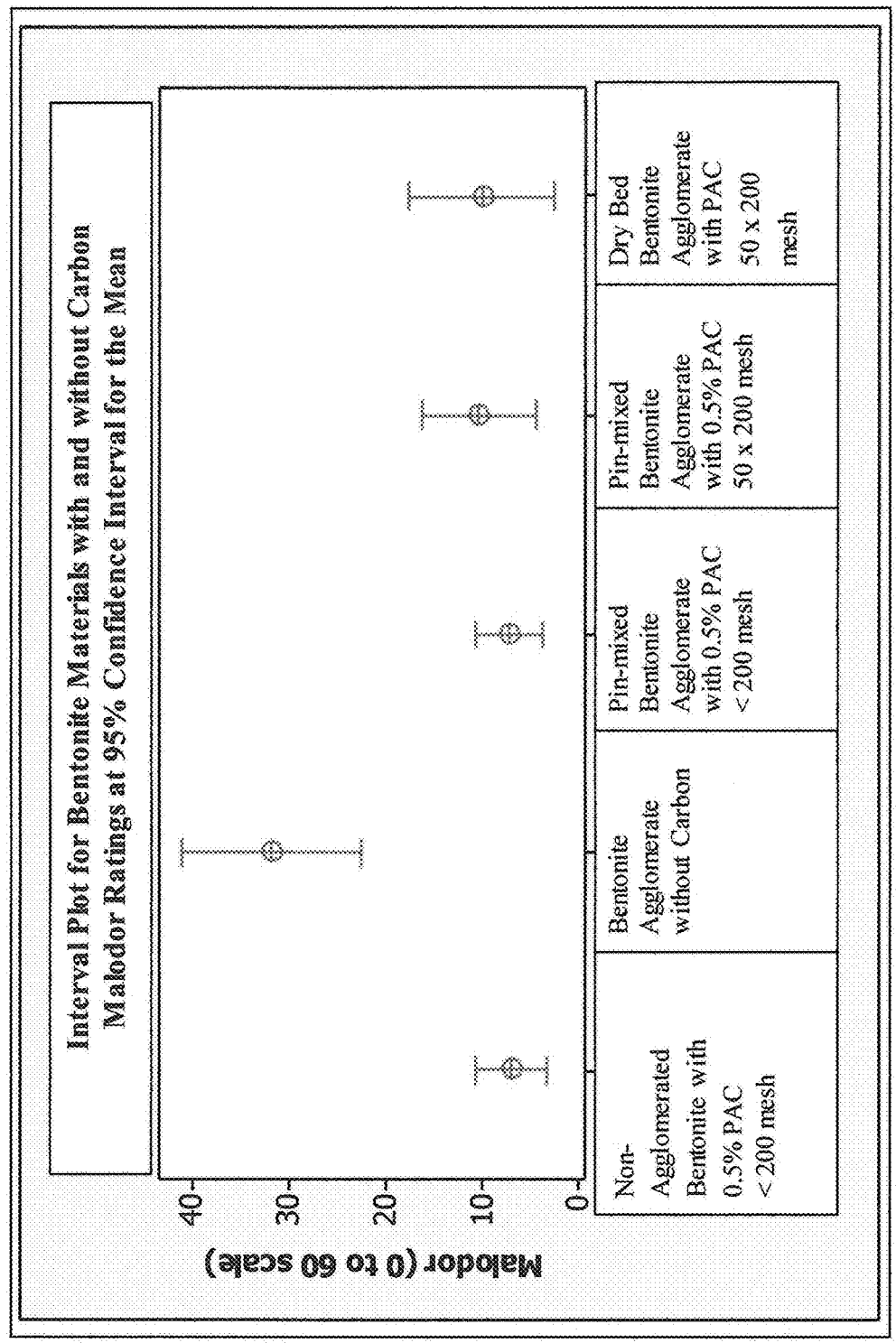

NON-VISIBLE ACTIVATED CARBON IN ABSORBENT MATERIALS

CROSS-REFERENCE TO RELATED APPLICATIONS

This application is a continuation of application Ser. No. 12/625,259 filed on Nov. 24, 2009, which is hereby incorporated by reference in its entirety.

FIELD OF THE INVENTION

The present invention relates to the use of Powdered Activated Carbon (PAC) in absorbent materials where odor absorption and/or odor reduction is desired. For instance, PAC may be used in combination with absorbent materials such as, clays, starches, cellulosic materials, agricultural waste products, and other suitable materials commonly found in animal litters for its odor-inhibiting properties. The present invention allows PAC to be combined with absorbent materials for odor-reduction without using color masking agents and without creating a black or grey product where the color of the PAC substantially impacts the visual appearance of the absorbent material.

RELATED ART

Clay has long been used as a liquid absorbent, and has found particular usefulness as an animal litter. Clay has very poor odor-controlling qualities, and inevitably waste build-up leads to severe malodor production. One attempted solution to the malodor problem has been the introduction of granular activated carbon (GAC) (20-8 mesh) into the litter. U.S. Pat. No. 5,860,391 to Maxwell et al. discloses the use of activated carbon in cat litter. The GAC exhibits very good performance with reducing odor in the litter, but it would be beneficial to have odor-reduction for a longer period of time than carbon with GAC allows. The addition of more GAC to an animal litter may improve odor-control but it is costly and at higher levels it is visible to consumers and gives the litter a grey or black appearance which is not desirable. To combat the black or gray appearance of the GAC a color masking agent may be used, but this also adds an additional cost and requires additional processing for the litter which is undesirable.

The use of activated carbon in litter is desirable for multiple reasons. First, there is the human objection to odor, but this is not the only reason that it is desirable to reduce odors. Secondly, studies have shown that cats prefer litter with little or no smell. One theory is that cats like to mark their territory by urinating. When cats return to the litterbox and don't sense their odor, they will try to mark their territory again. The net effect is that cats return to use the litter box more often if the odor of their markings is reduced.

U.S. Pat. No. 7,603,964 to Jenkins et al. discloses the use of PAC in cat litter, but it fails to teach how PAC can be incorporated into an animal litter without the use of color masking agents or without using an agglomeration processes to form composite particles where at least a portion of the PAC is positioned towards the center of the particle. The present invention teaches how to create an absorbent material with PAC which is substantially light-colored without using color masking agents or hiding the PAC materials in the center of an agglomerated absorbent material. This invention addresses the need in the field for an absorbent material with improved odor-controlling properties, that maintains such properties for longer periods of time and where the absorbent material maintains a light-colored appearance without the addition of color-masking agents.

SUMMARY OF THE INVENTION

We have discovered that by controlling the particle size of activated carbon within a specific range, it may be added at low levels without visibly darkening the material it is added to. If carbon particles are too large they may be easily seen. If the carbon particles are too small, they act as a pigment and create a very dark color to the entire material. By keeping the particle size below the resolving power of the human eye, and above the particle size which promotes surface coating, the carbon become almost invisible, contributing only a minor shift in shade.

One aspect of the invention includes an absorbent particulate composition comprising: (a) an agglomerated mixture of one or more absorbent materials suitable for use in an animal litter; and (b) powdered activated carbon having a particle size of about 50 to 700 microns; wherein the composition is substantially free of any color-masking agents and wherein the composition has a colorimetric rating of at least 55% white.

Another aspect of the invention includes an absorbent particulate composition comprising: (a) extruded particles comprising a mixture of one or more absorbent materials suitable for use in an animal litter; and (b) powdered activated carbon having a particle size of about 50 to 200 microns; wherein the composition is substantially free of any color-masking agents.

An additional embodiment of the invention includes an absorbent particulate composition comprising: (a) dry blended particles comprising a mixture of one or more absorbent materials suitable for use in an animal litter; and (b) powdered activated carbon having a particle size of about 50 to 200 microns; wherein the composition is substantially free of any color-masking agents.

Another aspect of the invention includes having one or more of the absorbent materials comprising absorbent clay selected from the group consisting of: bentonites, attapulgite, montmorillonite diatomaceous earth, Georgia White clay, sepiolite, slate, pumice, tobermite, marls, kaolinite, halloysite, smectite, hectorite, Fuller's earth and mixtures thereof. Another aspect of the invention includes having one or more of the absorbent materials be a cellulosic material made of plant products or by-products selected from the group consisting of: sawdust, waste-paper, wood, grains, hulls, nut shells, starches, fruit pulps, cotton, vegetables, nuts, trees, grasses, peat, and mixtures or combinations thereof.

A further aspect of the invention includes suitable methods for creating the absorbent materials compositions with PAC which include a pan agglomeration process, a high shear agglomeration process, a low shear agglomeration process, a high pressure agglomeration process, a low pressure agglomeration process, a rotary drum agglomeration process, a pan agglomeration process, a roll press compaction process, a pin mixer process, a dry blending process, a spray coating process, an extrusion process, a pelletizing process and a fluid bed process.

BRIEF DESCRIPTION OF THE DRAWINGS

For a fuller understanding of the nature and advantages of the present invention, reference should be made to the following detailed description read in conjunction with the accompanying drawing.

FIG. 1 is a graph illustrating the malodor ratings of embodiments of the present invention.

DETAILED DESCRIPTION

Before describing the present invention in detail, it is to be understood that this invention is not limited to particularly exemplified systems or process parameters as such may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "fragrance" includes two or more such fragrances.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. All numerical values, however, inherently contain certain errors necessarily resulting from the standard deviation found in their respective testing measurements.

The following description includes embodiments presently contemplated for carrying out the present invention. This description is made for the purpose of illustrating the general principles of the present invention and is not meant to limit the inventive concepts claimed herein.

The present invention relates generally to absorbent materials used in animal litter combined with PAC particles, with improved physical and chemical properties that are useful as an animal litter. The absorbent materials and PAC may be combined in a variety of different ways to form the absorbent material composition.

One method of forming an embodiment of the absorbent material composition of the present invention involves forming composites by agglomerating particles of an absorbent material(s) along with PAC without the addition of any color masking agents. In one embodiment of this invention, the PAC is combined with one or more absorbent materials in the agglomeration process. The combination of absorbent material(s), PAC, and/or additives or light-weighting materials by agglomeration will form a "composite particle" or "composites". In an alternative embodiment, the PAC may be applied to one or more absorbent materials after they have gone through an agglomeration process. The PAC can be applied by spraying the agglomerated particles with PAC and binder, dry blending or other suitable methods.

A fluid, e.g., water, or binder is usually added to the particles in the agglomerator. During the agglomeration process, the particles combine or coalesce to form composites. Controlled, predetermined agglomeration parameters are used to manipulate physical properties of the composites such as particle size, porosity, etc. The composites are then dried (if necessary) and collected. The agglomeration method includes, but is not limited to, a pan agglomeration process, a high shear agglomeration process, a low shear agglomeration process, a high pressure agglomeration process, a low pressure agglomeration process, a rotary drum agglomeration process, a pan agglomeration process and any combinations thereof. Specific embodiments of agglomeration processes will be set forth in more detail below.

Another method of forming an embodiment of the absorbent material composition of the present invention involves using an extrusion process. In the extrusion process one or more absorbent materials comprising one or more absorbent clays and/or cellulosic materials is extruded in to any desirable shape and combined with PAC. The combination of absorbent material(s), PAC, and/or additives or light-weighting materials by extrusion will form a "composite particle" or "composites". In one embodiment of this invention, the PAC is combined with one or more absorbent materials in the extrusion process. In an alternative embodiment, the PAC may be applied to one or more absorbent materials after they have gone through an extrusion process by spray coating with PAC and binder composition or by dry blending PAC with the extruded particles or other suitable methods for combining PACs with the extruded particles.

A third method involves using absorbent particles and PAC to form a dry blended absorbent material composition for use as an animal litter. In this embodiment, the PAC may be combined with one or more absorbent materials during the dry blending process or after the dry blending process where the blended absorbent particles are then sprayed with a PAC and binder composition.

Additional additives, such additives selected from the group consisting of antimicrobials, odor absorbers/inhibitors, binders, fragrances, litter filler materials, health indicating materials, nonstick release agents, superabsorbent materials, and mixtures thereof, may be added to any of these absorbent material compositions. In one embodiment of the invention, the absorbent material composition is substantially free of any color masking agents. In further embodiment of the present invention, the antimicrobial active is selected from the group consisting of boron containing compounds such as borax pentahydrate, borax decahydrate, boric acid, polyborate, tetraboric acid, sodium metaborate anhydrous, boron components of polymers, and mixtures thereof. Particles or compositions of one or more additives may be added to the absorbent material or composites of absorbent materials in an amount effective to perform the desired functionality or provide the desired benefit. These additives can be added during the agglomeration process so that the actives are incorporated by agglomeration into the composite itself, or can be added during a later processing step.

Light-weighting as defined herein means a material that causes a reduction in bulk density when compared to the bulk density of a comparably produced clay only material. Light-weighting materials may have other beneficial attributes in addition to providing for a decrease in bulk density. For example, as will be discussed in greater detail, composites containing expanded perlite stick less to the litter box when compared to their clay-only counterparts. Thus, light-weighting materials are one form of additives.

By using various processes described herein, such composites can be "engineered" to preferentially exhibit specific characteristics including but not limited to improved odor control, lower density, easier scooping, better particle/active consistency, higher clump strength, lower cost, etc. For example, an odor-controlling active distributed correctly may react with odor-causing volatile substances such that the resulting odor control is achieved using surprisingly low levels of active ingredient.

Absorbent Materials

As used herein particle size refers to sieve screen analysis by standard ASTM methodology (ASTM method D6913-04e1).

Absorbent materials may include cellulosic materials which are plant based materials or by-products of cellulosic materials, including but not limited to agricultural waste products and biomass materials. In addition to the traditional waste-paper and tree related sources for absorbent cellulosic materials, other materials useful materials for practicing the present invention include particulate matter derived from various plant sources, such as grains, fruits, cotton, vegetables, nuts, trees, grasses, peat, and the like. Representative cellulosic material sources from grains and starchy vegetables included but are not limited to, rice, rice hulls, wheat, corn, corn cobs and husks, barley, oats, quinoa, and other suitable starches and grains or by-products thereof. Exemplary cellulosic materials derived from fruits, include but are not limited to, citrus pulp (from lemons, oranges, grape-fruits, etc.), apple pulp, grape pulp, tomato pulp, and the like. Suitable cellulosic material sources from cotton include degraded cotton, cotton burns, cottonseed hulls, and the like. Additional, suitable cellulosic material sources from vegetables include beet pulp, carrot pulp, and the like. Suitable cellulosic materials sources derived from nuts include but are not limited to, peanut shells, walnut shells, pecan shells, almond shells, and the like. Representative cellulosic material sources from grasses include alfalfa, hay, straw, and the like.

Many liquid-absorbing clay materials may be used without departing from the spirit and scope of the present invention. Illustrative absorbent clay materials include but are not limited to bentonites, attapulgite, montmorillonite diatomaceous earth, Georgia White clay, sepiolite, slate, pumice, tobermite, marls, kaolinite, halloysite, smectite, hectorite, Fuller's earth, zeolites and mixtures thereof. Silica gels may also be used alone or in combination with one or more absorbent material, such as clays or cellulosic materials. Various embodiments of the present invention utilize clay materials having the following mean particle diameters: about 5000 microns or less; about 3000 microns or less; ranging from about 25 to about 150 microns.

Filler Materials

In addition to absorbent materials, filler materials such as limestone, sand, calcite, dolomite, recycled waste materials, zeolites, and gypsum can also be incorporated with the clay materials to reduce the cost of the litter without significantly decreasing the material's performance as a litter.

Because clays are heavy, it may be desirable to reduce the weight of the composites to reduce shipping costs, reduce the amount of material needed to fill the same relative volume of the litter box, and to make the material easier for customers to carry. Exemplary light-weighting materials include but are not limited to perlite, expanded perlite, volcanic glassy materials having high porosities and low densities, vermiculite, expanded vermiculite, pumice, silica gels, opaline silica, tuff, and lightweight agricultural byproducts. When selecting a light-weighting material, the effect the light-weighting material will have on the litter's performance is an important consideration. Factors to evaluate include how the light-weighting material will effect cost, ease of manufacture, clumping, tracking, absorbency, odor control, sticking to the box, dust, etc. In some cases, the light-weighting materials may also be performance-enhancing.

Various embodiments of the present invention utilize light-weighting materials having the following mean particle diameters: about 1500 microns or less; about 500 microns or less; ranging from about 1 to about 100 microns. Using the above lightweight materials, a bulk density reduction of 10-50% can be achieved relative to generally solid particles of the absorbent clay material (e.g., as mined). For example, composites in which sodium bentonite (Black Hills Bentonite, Mills, Wyo.) is the absorbent clay material (bulk density 67 lb/ft$^3$), using about 17% of expanded perlite, e.g., Kamco 5, (Kansas Minerals, Mancato, Kans.) having a bulk density of 5 lb/ft$^3$ results in up to a 53% bulk density reduction. Using roughly 13% of the 5 lb/ft$^3$ expanded perlite results in about a 43% reduction in bulk density. Using roughly 5% of the 5 lb/ft$^3$ expanded perlite results in about a 37% reduction in bulk density.

In addition to the light-weighting material chosen, the bulk density of the composites can be adjusted by manipulating the agglomeration process to increase or decrease pore size within the particle. Agglomeration parameters will be discussed in more detail below.

Heavyweight materials may be added to the light-weighted composite when it is desirable to have heavier particles. Heavy particles may be useful, for example, when the particles are used in an outdoor application in which high winds could blow the particles away from the target zone. Heavier particles also produce an animal litter that is less likely to be tracked out of a litter box. Illustrative heavyweight materials include but are not limited to sand, iron filings, etc.

Additives

Illustrative materials for the additives include but are not limited to antimicrobials, odor absorbers/inhibitors, binders, fragrances, health indicating materials, nonstick release agents, dedusting agents, superabsorbent materials, and mixtures thereof. In the embodiments of the present invention where composite particles are formed, of substantially every composite particle may contain PAC and/or additives, or in the case of a dry blend, the PAC and/or additives are substantially distributed throughout the final product.

Binders, such as, xanthan gum, acrylic polymer, natural and synthetic polymers, fibrillatable PTFE, or other binders known to those in the art could be used in place of water as the binder for combining absorbent materials and/or PAC. The composition may also include a binder such as water, lignin sulfonate (solid), polymeric binders, fibrillated Teflon® (polytetrafluoroethylene or PTFE), and combinations thereof. Useful organic polymerizable binders include, but are not limited to, carboxymethylcellulose (CMC) and its derivatives and its metal salts, guar gum cellulose, xanthan gum, starch, lignin, polyvinyl alcohol, polyacrylic acid, styrene butadiene resins (SBR), and polystyrene acrylic acid resins. Water stable particles can also be made with cross-linked polyester network, including but not limited to those resulting from the reactions of polyacrylic acid or citric acid with different polyols such as glycerin, polyvinyl alcohol, lignin, and hydroxyethylcellulose.

Dedusting agents can also be added to the particles in order to reduce the dust level. Many of the binders listed above are effective dedusting agents when applied to the outer surface of the composite absorbent particles. Other dedusting agents include but are not limited to gums, resins, water, and other liquid or liquefiable materials.

In one embodiment of the invention, the composition is substantially free of any color masking agents, dyes, pigments or the like. In an alternate embodiment of the invention, a dye, colorant, bleach, lightener, etc. may be added to vary the color of absorbent particles, such as to lighten the color of litter so it is more appealing.

Antimicrobial actives include, but are not limited to, boron containing compounds such as borax pentahydrate, borax decahydrate, boric acid, polyborate, tetraboric acid, sodium metaborate anhydrous, boron components of polymers, and mixtures thereof.

Superabsorbent materials can be used as an additive. Suitable superabsorbent materials include superabsorbent polymers such as AN905SH, FA920SH, and FO4490SH, all from Floerger. Preferably, the superabsorbent material can absorb at least 5 times its weight of water, and ideally more than 10 times its weight of water.

One type of odor absorbing/inhibiting active inhibits the formation of odors. An illustrative material is a water soluble metal salt such as silver, copper, zinc, iron, and aluminum salts and mixtures thereof. Zinc chloride, zinc gluconate, zinc lactate, zinc maleate, zinc salicylate, zinc sulfate, zinc ricinoleate, copper chloride, copper gluconate, and mixtures thereof are particularly effective. Other odor control actives include metal oxide nanoparticles. Additional types of odor absorbing/inhibiting actives include cyclodextrin, zeolites, activated carbon, acidic, salt-forming materials, and mixtures thereof.

Activated Carbon

Using a particle size of activated carbon within a specific range, it may be added at moderate levels without significantly darkening the absorbent material it is added to. If carbon particles are too large they may be easily seen. If the carbon particles are too small, they act as a pigment and create a very dark color to the entire material. But by keeping the particle size below the resolving power of the human eye, but above the particle size which promotes surface coating, the carbon become almost invisible, contributing only a minor shift in shade.

One critical problem with using activated carbon in litter is that depending upon the size of the activated carbon and the amount of the activated carbon in the litter composition; it may alter the color of the absorbent material giving it a black or grey appearance which is undesirable to consumers. Generally, the particle diameter of the carbon particles used in the invention is about 50 microns to about 700 microns (about 25 to 270 mesh). Illustrative desired particle size ranges include the following: about 25×100 mesh (about 150-700 microns), 35×200 mesh (about 75 to 550 microns), about 50×100 mesh (about 150 to 290 microns), and about 80×200 mesh (about 75 to 170 microns).

Unlike the prior art, the present invention teaches that it is not desirable to use smaller sized carbon particles with a size of less than 50 microns, or less than 45 microns, or less than 40 microns because the smaller particle size creates an undesirable increase in black dust and increases the black appearance of the litter. Conversely, a particle size of greater than 700 microns (about 25 mesh) is also undesirable because there is a decrease in performance on odor absorption and the appearance of larger sized black carbon particles is also more noticeable visually in the litter composition.

Embodiments of the present invention incorporate Powdered Activated Carbon (PAC) with one or more absorbent materials in a manner that preserves the light-color of the absorbent materials without the use of a color masking agent. PAC is defined as powdered material starting in the sub-micron size ranging up to about 80 mesh (180 microns; according to the ASTM) or 50 mesh (300 microns; according to the American Water Works Association). Granular activated carbon, or GAC is defined as larger than those same cutoffs that define PAC. Therefore, although PAC is generally used in these compositions, some GAC particle sizes (as defined by industry) can also be used.

The reason that this novel low-visibility effect works so well in the desired particle size range, is that the human eye can only resolve particles of about 350 microns (about 45 mesh) at 1 meter distance, or 700 microns (about 25 mesh) at 2 meter distance. The average person looking down at a cat box is able to see particles larger than 25 mesh, but would barely see particles between 25 and 35 mesh, and not be able to see particles less than 45 mesh at all. Keeping the particles below 25 mesh substantially reduces the ability to see the particles.

In order to maximize the rapid odor absorbing ability of the carbon, a smaller particle size range is also desired. This is because the smaller the particle, the higher the particles surface area available for absorption. However, if the particle is too small, it acts as a pigment, and even a small amount of material has the ability to coat surfaces black. We have discovered that my keeping the lower end of the particle size range to about 200 mesh (75 microns), we maintain the rapid odor absorbing ability of the carbon, while eliminating the pigmenting ability of the carbon.

Surprisingly, low levels of PAC about 0.01-5% by weight of the composition have been found to provide excellent odor control in cat litter when they are combined with absorbent materials. In addition, low levels of PAC not only provide excellent odor control but also will allow the absorbent materials to maintain their light colored appearance without having to include color masking agents. In one embodiment of the invention, PAC is present in the composition about 0.01-5%, or at about 0.05-5% or about 0.05-2%, or 0.05-1% or 0.05 to 0.3% by weight of the absorbent material composition. Using low levels of PAC is not only effective for odor control and maintaining a light colored absorbent material but it is also desirable from a cost-savings standpoint because one can use less PAC In one example of the invention, agglomerating small amounts of PAC particles with absorbent clay composites using water as binder results in litter materials with superior odor adsorbing performance. In this configuration, the PAC is highly effective at capturing malodorous volatile organic compounds as they escape from solid and liquid wastes due to the high surface area of the PAC, and its preferred location within the porous surfaces of the composites.

One potential drawback of using PAC is that it will tend to segregate out of the litter during shipping, thereby creating excessive dust (also known as "sifting"). In one embodiment of the invention, by agglomerating PAC or extruding PAC into the composites (or adding the PAC to the composites by a later processing step), the problems with carbon settling out during shipping is overcome. In other embodiments of the invention, the PAC may be added to one or more absorbent materials using a spray coating with a binder or fixing agent or it may be dry blended with the absorbent materials.

Methods of Making Absorbent Material Compositions

Methods for creating the composites, composite blends, and dry blends disclosed herein include, without limitation, a pan agglomeration process, a high shear agglomeration process, a low shear agglomeration process, a high pressure agglomeration process, a low pressure agglomeration process, a rotary drum agglomeration process, a mix muller process, a roll press compaction process, a pin mixer process, a batch tumble blending mixer process, an extrusion process and fluid bed processes. All of these are within the definition of "agglomeration" according to the invention.

Extrusion processes typically involve introducing a solid and a liquid to form a paste or doughy mass, then forcing through a die plate or other sizing means. Because the forcing of a mass through a die can adiabatically produce heat, a cooling jacket or other means of temperature regulation may be necessary. The chemical engineering literature has many examples of extrusion techniques, equipment and materials, such as "Outline of Particle Technology," pp. 1-6 (1999), "Know-How in Extrusion of Plastics (Clays) or NonPlastics (Ceramic Oxides) Raw Materials," pp. 1-2, "Putting Crossflow Filtration to the Test," *Chemical Engineering*, pp. 1-5 (2002), and Brodbeck et al., U.S. Pat. No. 5,269,962, especially col. 18, lines 30-61 thereof, all of which is incorporated herein by reference thereto. Fluid bed process is depicted in Coyne et al., U.S. Pat. No. 5,093,021, especially col. 8, line 65 to col. 9, line 40, incorporated herein by reference.

The agglomeration process in combination with the materials used allows the manufacturer to control the physical properties of particles, such as bulk density, dust, strength, as well as particle size distribution (PSD) without changing the fundamental composition and properties of the component particles.

Generally, absorbent clay particles (e.g., bentonite powder) are mixed with other absorbent materials (e.g. absorbent clays, cellulosic materials) and/or filler materials (e.g. light-weighting particles) to form a dry mixture, which is stored in a hopper or feeder. The mixture is fed with optional wetting from the hopper into an agglomerating apparatus. Alternatively, the clay particles, cellulosic materials and/or light-weighting particles may be fed individually from separate hoppers. The particles of activated carbon (e.g., PAC) may optionally be dry blended with either the clay or light-weighting particles or added to the mixture at this time. Alternatively, the particles of active can be stored in another hopper, from which they are fed into the agglomerator. Water and/or binder is sprayed onto the particles in the agglomerating apparatus via sprayers to raise/maintain the moisture content of the particles at a desired level so that they stick together. Some clays, e.g., bentonite, act as its own binder when wetted, causing it to coalesce, so additional binder may not be necessary if the percentage of bentonite used is high enough. Liquid additives or solid additives (e.g. PAC) may physically suspended in a slurry can be added by a sprayer during one of the processes described or as a later step after agglomeration, extrusion, dry blending etc. has already occurred.

Depending on the agglomeration parameters chosen, the composites tumble off upon reaching a certain size. At this point, i.e., prior to drying, if a drying step is employed, the particles typically have a high enough moisture content that they are malleable and can be formed into any desired shape. If the composites are substantially spherical in shape when they leave the agglomerator, such as with pan agglomeration, molding, compaction, or other processes known in the art, can transform them into non-spherical shapes such as, for example, ovals, flattened spheres, hexagons, triangles, squares, etc. and combinations thereof. The composites are then dried, if necessary, to a desired moisture level by any suitable mechanism, such as a rotary or fluid bed drier.

In one embodiment, the moisture content of the composites is less than about 15% by weight, generally in the range of 8-13% by weight. At the outlet of the dryer, the particles are screened with sieves or other suitable mechanism to separate out the particles of the desired size range. In another embodiment, e.g., roll pressing, no drying is necessary, but the agglomerates are fed into a grinder after the agglomerator to form composites of suitable size which are then screened as described above. In one embodiment, the selected particle size range is about 10 mm to about 100 microns. In another embodiment, the size range is about 2.5 mm to about 100 microns. Preferred particle sizes for use as animal litter are in 12×40 mesh (1680-400 microns) range. The exhaust from the dryer is sent to a baghouse for dust collection.

Alternatively, the activated carbon can be physically dispersed along pores of an agglomerated composite by suspending an insoluble active in a slurry and spraying the slurry onto the particles. The suspension travels into the pores and discontinuities, depositing the active therein.

Additional additives such as borax and fragrance can be added to the particles at any point in the process before, during and/or after agglomeration. Also, additional/different actives can be dry blended with the particles.

Pan Agglomeration

The pan agglomeration process intrinsically produces agglomerates with a narrow particle size distribution (PSD). The PSD of the agglomerates can be broadened by utilizing a pan agglomerator that continuously changes angle (pivots back and forth) during the agglomeration process. For instance, during the process, the pan could continuously switch from one angle, to a shallower angle, and back to the initial angle or from one angle, to a steeper angle, and back to the initial angle. This variable angle process would then repeat in a continuous fashion. The angles and rate at which the pan continuously varies can be specified to meet the operator's desired PSD and other desired attributes of the agglomerates.

Pan agglomeration manipulation and scale-up can be achieved through an empirical relationship describing the particle's path in the pan. Process factors that impact the path the particle travels in the pan include but are not limited to pan dimensions, pan speed, pan angle, input feed rate, solids to process liquid mass ratio, spray pattern of process liquid spray, position of scrapers, properties of solids being processed, and equipment selection. Additional factors that may be considered when using pan agglomeration include particle to particle interactions in the pan, gravity effects, and the following properties of the particles in the pan: distance traveled, shape of the path traveled, momentum, rotational spin about axis, shape, surface properties, and heat and mass transfer properties. A more detailed description of the benefits of the pan agglomeration process is contained in pending U.S. application Ser. Nos. 11/929,018 filed Oct. 30, 2007 and 12/032,450 filed Feb. 15, 2008 and owned by the same assignee. Pending U.S. application Ser. Nos. 11/929,018 and 12/032,450 are hereby incorporated by reference in its entirety. U.S. Pat. No. 7,603,964 filed Apr. 29, 2005, owned by the same assignee, is hereby incorporated by reference in its entirety.

In one embodiment of the invention, a pan agglomeration process for forming composites is employed. Absorbent particles, PAC and optionally filler materials and optional additives are fed to a pan agglomerator. Water is sprayed onto the particles via a sprayer in the agglomerator. The agglomerated composites are then dried in a dryer and sorted by size in a sieve screen system. One draw back to the pan agglomeration, is that the light-weighting material tends to blow away when first added to the pan resulting in a need to use more starting material than theoretically calculated. One way of alleviating this problem is to "protect" the light-weighting material by first blending it with a small amount of heavier clay material. This can be accomplished in a variety of ways including any kind of mixing apparatus, e.g., a pin mixer.

Pin/pan Agglomeration

An alternative process employs pin/pan agglomeration process for forming composites. Absorbent particles, PAC and optionally filler materials and optional additives are fed to a pin mixer. The pin/pan process enables the filler material (e.g. light-weighting material) to first be blended with the absorbent materials in order to "weigh down" the light-weighting material by forming small "dedusted particle mixtures" which are then fed into a pan agglomerator where they are agglomerated and dried in a dryer. It should be noted that almost any kind of mixing apparatus could be used in place of the pin mixer. The dry unsieved agglomerates are sorted in a screener to produce composites in the desired size range. The pin mixer upstream from the pan minimizes dust issues that are often encountered when feeding dry powders to a pan agglomerator exclusively. The pin/pan agglomeration process creates composites that are highly porous and have a relatively narrow particle size distribution. The process has a large capacity per unit operation and is relatively easy to scale up.

Roll-press

An additional process that may be used to create the absorbent material composition uses a roll press process for forming composites. Absorbent particles, PAC, and optional filler materials and optional additives are fed to a roll press and agglomerated through applied external forces in dies. The agglomerated composites travel through a flake breaker which grinds them to form smaller-sized composites. The composites are then sized with a sieve screen. The roll-press requires little to no water addition and therefore no drying is necessary which significantly reduces operating costs. The process is stable, robust and can be automated.

Pin-mixer

Another exemplary processes uses a pin mixer process for forming composites. Absorbent particles, activated carbon, optional filler materials and optional additives are fed to a pin mixer. Water and optional binders are also sprayed into the mixer; the random particle dynamics in the mixer allow for both mixing and agglomeration of the particles into composites. The agglomerated composites are then dried in a dryer and sorted by size in a sieve screen system. The pin-mixer uses less moisture that the pan or pin/pan combination has a large capacity per unit of operation, and automated control is possible.

Mix-muller

A further exemplary process employs a mix muller process for forming composites. The various components including clay particles, PAC, optional filler materials and optional additives and water and/or binder are added to a pellegrini mixer. The damp mixture is sent to a muller agglomerator where the mixture is agglomerated with some pressure applied but typically not as much as with a roll press. The agglomerated particles are dried in a dryer, processed in a flake breaker, and then sorted by size in a sieve screen system.

Material Properties and Testing Methods

Illustrative composites after drying have a specific weight of from about 0.15 to about 1.2 kilograms per liter and a liquid absorbing capability of from about 0.6 to about 2.5 liters of water per kilogram of particles. In one embodiment of the present invention, the composites absorb about 50% or more of their weight in moisture. In another embodiment of the present invention, the composites absorb about 75% or more of their weight in moisture. In a further embodiment of the present invention, the composites absorb greater than approximately 80% of their weight in moisture. In another embodiment of the present invention, the composites absorb about 90% or more of their weight in moisture.

Examples of materials that can be fed to the agglomerator using the processes of FIGS. 2-6 include:

0-100% Bentonite Powder & 0-5% PAC 85-99% Bentonite Powder, 1-15% Expanded Perlite, & 0-5% PAC 45-90% Bentonite Powder, 10-55% Mounds Clay, & 0-5% PAC 75-90% Bentonite Powder, 10-25% Georgia White Clay (GWC), & 0-5% PAC 60-70% Bentonite Powder, 30-40% Sand, & 0-5% PAC 70-80% Bentonite Powder, 20-30% Zeolite, & 0-5% PAC Table 1 lists illustrative properties for various compositions of bentonite-based agglomerated composites. In all cases the balance of material is bentonite clay.

TABLE 1

| Percentage Expanded Perlite | Percentage PAC | Moisture Addition to Feed (wt %) | Agglomeration Process | Bulk Density (lb/ft$^3$) | % Bulk Density Reduction |
|---|---|---|---|---|---|
| 0 | 0.54 | 0 | Roll Press 2000 psi | 61 | 10 |
| 0 | 0.54 | 10 | High shear mixer | 47 | 31 |
| 5 | 0.51 | 15 | High shear mixer | 37 | 46 |
| 14 | 0.51 | 15 | High shear mixer | 31 | 54 |
| 14 | 0.46 | 10 | Roll Press 300 psi | 57 | 16 |
| 28 | 0.39 | 9 | Roll Press 200 psi | 50 | 26 |
| 42 | 0.31 | 13 | Roll Press 100 psi | 43 | 37 |
| 14.4 | 0.54 | 45 | Pin/Pan combination | 31 | 54 |
| 17.1 | 0.54 | 50 | Pin/Pan combination | 32 | 53 |
| 13.4 | 0.54 | 40 | Pin/Pan combination | 41 | 40 |
| 13.4 | 0.54 | 40 | Pin/Pan combination | 39 | 43 |
| 13.4 | 0.54 | 40 | Pin/Pan combination | 41 | 40 |
| 13.4 | 0.54 | 33 | Pin/Pan combination | 35 | 49 |
| 13.4 | 0.1 | 35 | Pin/Pan combination | 38 | 44 |
| 13.4 | 0.1 | 35 | Pin/Pan combination | 37 | 46 |

TABLE 1-continued

| Percentage Expanded Perlite | Percentage PAC | Moisture Addition to Feed (wt %) | Agglomeration Process | Bulk Density (lb/ft³) | % Bulk Density Reduction |
|---|---|---|---|---|---|
| 13.4 | None | 40 | Pin/Pan combination | 39 | 43 |

Clump Strength

Clump strength is measured by first generating a clump by pouring 10 ml of pooled cat urine (from several cats so it is not cat specific) onto a 2 inch thick layer of litter. The urine causes the litter to clump. The clump is then placed on a ½" screen after a predetermined amount of time (e.g., 6 hours) has passed since the particles were wetted. The screen is agitated for 5 seconds with the arm up using a Ro-Tap Mechanical Sieve Shaker made by W.S. Tyler, Inc. The percentage of particles retained in the clump is calculated by dividing the weigh of the clump after agitation by the weight of the clump before agitation. Referring again to the table above, note that the clump strength indicates the percentage of particles retained in the clump after 6 hours. As shown, >90%, and more ideally, >95% of the particles are retained in a clump after 6 hours upon addition of an aqueous solution, such as deionized water or animal urine. Note that ≥about 80% particle retention in the clump is preferred.

Malodor Rating

The composites disclosed herein provide meaningful benefits, particularly when used as an animal litter that include but are not limited to improvements in final product attributes such as odor control, litter box maintenance benefits, reduced dusting or sifting, and consumer convenience. As such, the following paragraphs shall discuss the composites in the context of animal litter, it being understood that the concepts described therein apply to all embodiments of the composites.

Significant odor control improvements over current commercial litter formulas have been identified for, but are not limited to, the following areas:

Fecal odor control (malodor source: feline feces)
Ammonia odor control (malodor source: feline urine)
Non-ammonia odor control (malodor source: feline urine)

Odor control actives that can be utilized to achieve these benefits include but are not limited to powdered activated carbon, granular activated carbon, silica powder (Type C), borax pentahydrate, and bentonite powder.

Because of the unique processing of the composites of the present invention, lower levels of active are required to effectively control odors. In the case of carbon, the effective amount present is 5% or less based on the weight of the particle. In illustrative embodiments, the carbon is present in the amount of 1.0% or less, 0.5% or less, and 0.3% or less, based on the weight of the particle. This lower amount of carbon significantly lowers the cost for the particles, as carbon is very expensive compared to clay. The amount of carbon required to be effective is further reduced because the agglomeration process incorporates the carbon into each particle, using it more effectively. In the case of composite blends, carbon is present in substantially every other particle or every third particle (depending on the composition of the blend).

Table 2 shows the malodor rating for exemplary compositions of the present invention in comparison with compositions comprising PAC at a smaller size range and compositions without activated carbon. In this test, a lab-based method was used to objectively measure the absorptive capacity of the carbons. A known cat waste odor component was introduced in equal amounts as a vapor to the carbon test samples in a closed container. The odor was absorbed by the test samples, and the remaining odor not absorbed was present in the headspace and measured. The remaining odor can be measured by a variety of techniques such as gas chromatography, gas analysis indicator tubes (Draeger tubes), an electronic nose, or Infrared Analysis. The percentage of odor absorbed is expressed on a 0-100% scale, calculated as the measured value divided by the value of a blank sample. The higher the value, the better the odor control. The results in Table 2 show that PAC in both sizes provides excellent odor absorption even at very low levels.

TABLE 2

| % Carbon | % Odor Absorbed |
|---|---|
| 0% Carbon (control) | 0% |
| 0.1 g PAC as −200 mesh powder | 97.5% |
| 0.1 g PAC as 50 × 200 mesh | 98.3% |
| 0.1 g carbon as graphite flake (control) | 0% |
| 0.1 g Gypsum (CaSO$_4$ 2H$_2$O) (control) | 11.5% |

FIG. 1 illustrates the sensory malodor ratings for the animal litter compositions contained in Table 3 below. In this test, a human-based Malodor Sensory Method was used to realistically measure the odor neutralizing ability of the carbons. Real cat waste was used in equal amounts between each sample, and the samples were dosed for four days. Trained human panelists then evaluate the amount of malodor that is left in each sample. The percentage of odor absorbed is expressed on a 0-60 point scale, the lower, the better the odor control. Two separate sessions were conducted to evaluate each sample. The sessions were averaged and the results plotted graphically in FIG. 1. All samples containing carbon had 0.5% by weight of PAC. There was a control sample (sample C) of a bentonite agglomerate without carbon. FIG. 1 shows that the two different kinds of agglomerate samples with 50×200 mesh PAC had a similar malodor performance with the agglomerate samples with PAC at less than 200 mesh. Therefore one can see that the low-visibility PAC (50×200 mesh) surprisingly has very good odor control performance while creating a very small appearance change to the absorbent material with the addition of carbon.

TABLE 3

| Sample | PAC (wt. %) | PAC Particle Size (microns) | Malodor Rating (Scale 0-60) |
|---|---|---|---|
| A | 0.5% | Less than 75 microns (<200 mesh) | 7 |
| B | 0.0% | N/A | 32 |
| C | 0.5% | Less than 75 microns (<200 mesh) | 7 |
| D | 0.5% | 75 to 300 microns (50 × 200 mesh) | 10 |
| E | 0.5% | 75 to 300 microns (50 × 200 mesh) | 9 |

In summary, composites containing PAC of either size are not significantly different from each other in malodor, averaging between 7 and 10 units, and ranging from 2 to 17 units, as determined by the Malodor Sensory Method. Whereas the control that does not contain carbon is significantly higher, with a rating of about 32, ranging between 22 and 42.

Description of Malodor Sensory Method:
1. Cat boxes are filled with 2,500 cc of test litter.
2. Boxes are dosed each morning for four days with 30 g of pooled feces.

3. On the fourth day the center of each box is dosed with 20 ml pooled urine.
4. The boxes are positioned into sensory evaluation booths.
5. The boxes are allowed to equilibrate in the closed booths for 30-45 minutes before panelist evaluation.
6. The samples are then rated on a 60 point line scale by trained panelists.

The agglomerated mixture of clay and activated carbon exhibit noticeably less odor after four days from contamination with animal waste as compared to agglomerated particles of clay alone or blends of agglomerated particles of clay and non-agglomerated particles of clay under substantially similar conditions.

Colorimetric Data

Table 4 shows absorbent material compositions with PAC and without PAC and with PAC at a desirable mesh size and at an undesirable mesh size. The colorimetric measurements are provided on a scale of 0-100 where 0 is the most black and 100 is the most white. The results are then reported as a percentage of black and percentage of white which together equal 100%.

The information in Table 4 shows that there is a dramatic shift in visual appearance of the absorbent materials when PAC is added in the size range of 50×200 mesh vs. when PAC is added which about −200 mesh. The color shift from a clay absorbent animal litter without PAC, to PAC having a size of −200 mesh, is about 33-47% shift in color. Conversely, the composition with PAC having a mesh size of 50×200 only created a 6-8% color shift in comparison to the clay litter without carbon. The human eye can only detect color shifts of about 3% or more so a 6-8% color shift only has a slight appearance of being darker. To please consumers, it is desirable to preserve the light colored appearance of the absorbent materials so it is beneficial to use PAC in the size range of 50-700 microns. The addition of PAC in range of 50-200 microns to an absorbent material only creates a color change shift of less than 30%. In one embodiment of the invention, the color change to the base material to the base material plus PAC is less than 20%, preferably less than 15%, more preferably less than 10%. Using PAC at the appropriate size, 50-200 microns, and weight percentage, 0.01-5% by wt of the absorbent material composition, allows one to make an absorbent material composition which is substantially white in color without the addition of color masking agents to whiten the carbon in the absorbent materials.

TABLE 4

| Base Material | Activated Carbon (wt. %) | Resulting Color | % White | % Change in White Value | % Black | % Change in Black Value |
|---|---|---|---|---|---|---|
| Zeolite | 0% carbon (control) | White | 75% | — | 25% | — |
| Zeolite | 1% carbon as 50 × 200 mesh | Off-white | 63% | 12% | 37% | 12% |
| Zeolite | 1% carbon as −200 mesh | Black | 28% | 47% | 72% | 47% |
| Attapulgite | 0% carbon (control) | Off-white | 68% | — | 32% | — |
| Attapulgite | 1% carbon as 50 × 200 mesh | Off-white | 62% | 6% | 38% | 6% |
| Attapulgite | 1% carbon as −200 mesh | Dark Grey | 35% | 33% | 65% | 33% |

Exemplary Absorbent Litter Compositions

The following sample litter compositions are included to show different kinds of potential litter compositions which are within the scope of the present invention. The following examples are intended to be illustrative of the present invention an do represent a comprehensive list of compositions covered by the claims of the application. The breadth and scope of a preferred embodiment should not be limited by any of the below-described exemplary embodiments, but should be defined only in accordance with the following claims and their equivalents

EXAMPLE 1

0.5% 30×100 mesh activated carbon
99.5% Sodium Bentonite
Agglomerated by a pin mixer and a pan into an agglomerated particle

EXAMPLE 2

0.4% 60×200 mesh activated carbon
0.3% sodium tetraborate pentahydrate
99.3% Attapulgite granules; Granules sprayed with 0.5% load of a 10% tacky acrylic adhesive
Ingredients dry mixed together

EXAMPLE 3

1% 50×200 mesh activated carbon
0.5% sodium tetraborate decahydrate
1% guar gum
97.5% pine chips
Ingredients dry mixed together.

Alternative Uses for Absorbent Compositions

As mentioned above, the composites have particular application for use as an animal litter. The litter would then be added to a receptacle (e.g., litterbox) with a closed bottom, a plurality of interconnected generally upright side walls forming an open top and defining an inside surface. However, the particles should not be limited to animal litters, but rather could be applied to a number of other applications such as:

Litter Additives—Formulated product can be pre-blended with standard clumping or non-clumping clays to create a less expensive product with some of the benefits described herein. A post-additive product could also be sprinkled over or as an amendment to the litter box.

Filters—Air or water filters could be improved by either optimizing the position of actives into areas of likely contact, such as the outer perimeter of a filter particle. Composites with each subcomponent adding a benefit could also be used to create multi-functional composites that work to eliminate a wider range of contaminants.

Bioremediation/Hazardous/Spill Cleanup—Absorbents with actives specifically chosen to attack a particular waste material could be engineered using the technology described herein. Exemplary waste materials include toxic waste, organic waste, hazardous waste, and non-toxic waste.

Pharma/Ag—Medications, skin patches, fertilizers, herbicides, insecticides, all typically use carriers blended with actives. Utilization of the technology described herein reduce the amount of active used (and the cost) while increasing efficacy.

Soaps, Detergents, and other Dry Products—Most dry household products could be engineered to be lighter, stronger, longer lasting, or cheaper using the technology as discussed above.

Mixtures of Different Particles—The composites can be dry mixed with other types of particles, including but not limited to other types of composites, extruded particles, particles formed by crushing a source material, etc. Mixing composites with other types of particles provides the benefits provided by the composites while allowing use of lower cost materials, such as crushed or extruded bentonite. Illustrative ratios of composites to other particles can be 75/25, 50/50, 25/75, or any other ratio desired. For example, in an animal litter created by mixing composites with extruded bentonite, a ratio of 50/50 will provide enhanced odor control, clumping and reduced sticking, while reducing the weight of the litter and lowering the overall cost of manufacturing the litter.

Mixtures of Composites with Actives—The composites can be dry mixed with actives, including but not limited to particles of activated carbon.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

We claim:

1. A mixture of discrete solid particles suitable for use as an animal litter comprising:
   (a) one or more absorbent materials suitable for use in an animal litter; and
   (b) activated carbon ranging in size from 75-700 microns in an amount from about 0.5% to about 5% by weight of the mixture;
   wherein a random and relatively consistent particle distribution of discrete particles of the one or more absorbent materials and discrete particles of the activated carbon exists throughout the mixture and the mixture does not contain any composite particles of the one or more absorbent materials and the activated carbon; and
   wherein the mixture is substantially free of any color-masking agents; and
   wherein the mixture has a color change of less than 20% as compared to the one or more absorbent materials.

2. The mixture recited in claim 1, wherein said activated carbon ranging in size from 75-700 microns is present in an amount from 0.5% to 1% by weight of the mixture.

3. The mixture recited in claim 1, wherein said one or more absorbent materials suitable for use in an animal litter ranges in size from 420 to 1680 microns (12 to 40 mesh).

4. The mixture recited in claim 1, wherein the activated carbon ranges in size from 75 to 500 microns.

5. The mixture recited in claim 1, wherein the mixture has a color change of less than 15% as compared to the one or more absorbent materials.

6. The mixture recited in claim 1, wherein the mixture has a color change of less than 10% as compared to the one or more absorbent materials.

7. The mixture recited in claim 1, wherein the activated carbon ranges in size from 75 to 300 microns.

8. The mixture recited in claim 2, wherein the mixture has a color change of less than 15% as compared to the one or more absorbent materials.

9. The mixture according to claim 1, wherein one or more of the absorbent materials is an absorbent clay selected from the group consisting of: bentonites, attapulgite, montmorillonite diatomaceous earth, Georgia White clay, sepiolite, slate, pumice, tobermite, marls, kaolinite, halloysite, smectite, hectorite, Fuller's earth and mixtures thereof.

10. The mixture recited in claim 9, wherein said particles of absorbent clay are about 5000 microns or less.

11. The mixture according to claim 1, wherein one or more of the absorbent materials is a cellulosic material made of plant products or by-products selected from the group consisting of: sawdust, waste-paper, wood, grains, hulls, nut shells, starches, fruit pulps, cotton, vegetables, nuts, trees, grasses, peat, and mixtures or combinations thereof.

12. The mixture recited in claim 11, wherein said particles of cellulosic materials are about 1500 microns or less.

13. The mixture recited in claim 1, further comprising an additive selected from the group consisting of antimicrobials, odor absorbers/inhibitors, binders, fragrances, litter filler materials, health indicating materials, nonstick release agents, superabsorbent materials, and mixtures thereof.

14. The mixture recited in claim 13, wherein said antimicrobial active is selected from the group consisting of boron containing compounds such as borax pentahydrate, borax decahydrate, boric acid, polyborate, tetraboric acid, sodium metaborate anhydrous, boron components of polymers, and mixtures thereof.

15. The mixture recited in claim 1, wherein the mixture has a colorimetric rating of at least 55% white.

16. The mixture recited in claim 1, wherein the mixture has a colorimetric rating of at least 60% white.

17. The mixture recited in claim 2, wherein the mixture has a colorimetric rating of at least 55% white.

18. The mixture recited in claim 2, wherein the mixture has a colorimetric rating of at least 60% white.

* * * * *